(12) United States Patent
Blackwell et al.

(10) Patent No.: US 8,440,740 B2
(45) Date of Patent: May 14, 2013

(54) DENTAL GLASS COMPOSITIONS UTILIZING A GLASS IONOMER AND AN ACIDIC COPOLYMER

(75) Inventors: Gordon Blackwell, Constance (DE); Stefan Brugger, Radolfzell (DE); Denise Achilles, Constance (DE); Jorg Kempter, Constance (DE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 12/814,598

(22) Filed: Jun. 14, 2010

(65) Prior Publication Data

US 2011/0071233 A1   Mar. 24, 2011

(51) Int. Cl.
*A61K 6/00*     (2006.01)
*C08F 2/50*     (2006.01)

(52) U.S. Cl.
USPC .......................................................... 523/116

(58) Field of Classification Search .................... 523/116
See application file for complete search history.

(56) References Cited

U.S. PATENT DOCUMENTS

| | | | | | |
|---|---|---|---|---|---|
| 4,016,124 | A | * | 4/1977 | Crisp et al. | 523/116 |
| 4,358,549 | A | * | 11/1982 | Randklev | 523/117 |
| 4,524,824 | A | * | 6/1985 | Shimokobe et al. | 106/35 |
| 4,591,384 | A | * | 5/1986 | Akahane et al. | 106/35 |
| 4,678,436 | A | * | 7/1987 | Kondo et al. | 433/228.1 |
| 4,758,612 | A | * | 7/1988 | Wilson et al. | 524/5 |
| 4,775,592 | A | * | 10/1988 | Akahane et al. | 428/406 |
| 4,814,362 | A | * | 3/1989 | Billington et al. | 523/117 |
| 4,900,697 | A | * | 2/1990 | Akahane et al. | 501/57 |
| 4,927,866 | A | * | 5/1990 | Purrmann et al. | 523/115 |
| 5,215,459 | A | * | 6/1993 | Ney et al. | 433/215 |
| 5,338,773 | A | * | 8/1994 | Lu et al. | 523/116 |
| 5,641,347 | A | * | 6/1997 | Grabowski et al. | 106/35 |
| 5,883,153 | A | * | 3/1999 | Roberts et al. | 523/116 |
| 2007/0043142 | A1 | * | 2/2007 | Dodiuk-Kenig et al. | 523/116 |
| 2010/0152318 | A1 | * | 6/2010 | Blackwell | 523/116 |

FOREIGN PATENT DOCUMENTS

| | | | |
|---|---|---|---|
| GB | 1304987 | * | 3/1971 |
| GB | 1304987 | | 4/1974 |
| WO | 2006050829 A1 | | 5/2006 |
| WO | WO 2006050829 A1 | * | 5/2006 |

* cited by examiner

Primary Examiner — James J Seidleck
Assistant Examiner — Peter A Salamon

(74) *Attorney, Agent, or Firm* — David A. Zdurne; Douglas J. Hura; Leana Levin

(57) ABSTRACT

A hardening composition comprising a particulate glass, said glass comprising 10-35% by weight of silica, 10-35% by weight of alumina, 3-30% by weight of zinc oxide, 4-30% by weight of $P_2O_5$ and 3-25% by weight of fluoride, and an acidic copolymer reactive with the particulate glass under aqueous conditions. An aqueous polymer solution comprising 10 to 65% by weight of the acidic copolymer of the hardening composition with a mean molecular weight of from 50,000 to 200,000, obtainable by a process comprising the copolymerization of a mixture containing acrylic acid and an acrylic acid ester (I) and/or a compound of the formula (II) and, optionally, a compound of the formula (III):

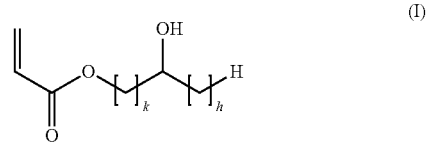

(I)

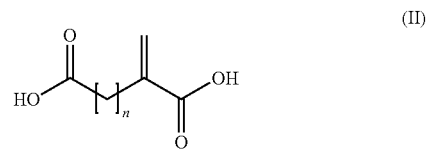

(II)

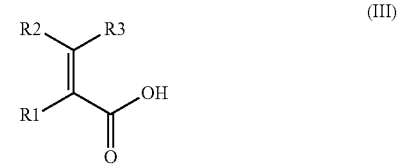

(III)

wherein k is an integer of from 1 to 5; h is an integer from 0 to (5−k); n is an integer of from 1 to 3; R1 is hydrogen or a C1-6 alkyl group, and; R2 and R3 independently represent hydrogen, a C1-6 alkyl group or a moiety of the following formula (IV):

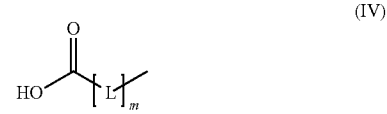

(IV)

wherein m independently is an integer of from 0 to 3, and L is —$CH_2$— or —CH=CH—; provided that at least one of R1, R2 or R3 is not hydrogen.

32 Claims, No Drawings

US 8,440,740 B2

DENTAL GLASS COMPOSITIONS UTILIZING A GLASS IONOMER AND AN ACIDIC COPOLYMER

FIELD OF THE INVENTION

The present invention relates to hardening composition comprising a particulate glass and an acidic copolymer reactive with the particulate glass under aqueous conditions. Furthermore, the present invention also relates to an aqueous polymer solution comprising 10 to 65% by weight of a specific acidic copolymer. A hardened glass ionomer obtained based on a glass ionomer hardening composition of the present invention, in particular by using the aqueous polymer solution according to the invention, has improved mechanical properties such as biaxial flexural strength, fracture toughness and compressive strength.

BACKGROUND OF THE INVENTION

Glass ionomers used as dental restoratives have advantages over conventional resin containing composites and conventional resin reinforced glass ionomer restoratives for several reasons. For example, glass ionomers are tolerant to application on wet surfaces, have low shrinkage and are self-adhesive. For these reasons, they are said to, be easy and forgiving to use. Also, since glass ionomers contain polymers rather than monomers, there is no risk of acrylic monomers leaching out, which can lead to sensitization and allergic reactions. Furthermore, glass ionomers bond chemically to dental hard tissues, and may also provide a beneficial level of fluoride release, which helps to prevent recurrent caries.

A key weakness of commercial glass ionomers, however, is their relatively low biaxial flexural strength of only up to about 45 MPa, and low fracture toughness of only about 0.5 MPa·m$^{1/2}$ which may lead to fracture at the edges of a restoration and, in the worst case, to bulk fracture of a restoration.

The inferior mechanical properties of conventional glass ionomers limit the range of application. Moreover, the inferior mechanical properties of conventional glass ionomers may lead to catastrophic failure when used as a dental restoration, such that the lifetime of the restoration may be significantly shortened.

A second problem with conventional glass ionomer hardening compositions is the stability of the polymer solution used. At the high concentrations needed to obtain sufficient strength, the polymer solutions tend to gel on storage and cannot then be mixed with a particulate glass powder.

A third problem is that the viscosity of the polymer solutions used in glass ionomer hardening compositions increases with increase in molecular weight, so that with high molecular weight polymers the polymer solution and particulate glass powder become hard to mix.

Yet a further problem is that many glasses presently available for use in glass ionomer formulations are too reactive towards acid and do not provide a long enough working time when ground to the required fine particle size.

U.S. Pat. No. 4,758,612 describes a dental cement containing a particulate aluminosilicate glass and a water soluble polymer having an average molecular weight from 1000 to 1,000,000, preferably from 10,000 to 25,000. Copolymers of acids such as acrylic acid, aconitic acid, itaconic acid, or citraconic acid are suggested for use in the invention.

It is the problem of the present invention to provide a hardening composition comprising a particulate glass and an acidic copolymer reactive with the particulate glass under aqueous conditions, wherein the acidic copolymer may either be
 (i) dissolved in water to form an aqueous solution of the acidic copolymer in high concentration which has high stability during storage and may be easily mixed with a particulate glass powder or with an admixture of particulate glass and dried copolymer (a glass ionomer powder), or
 (ii) dried and mixed with a particulate glass to provide a glass ionomer powder
and wherein the glass ionomer hardening composition sets or hardens to form a hardened glass ionomer which provides improved mechanical properties over conventional glass ionomers, in particular increased biaxial flexural strength and fracture toughness, $K_{Ic}$.

It is a further problem of the present invention to provide an acidic copolymer solution of the required high molecular weight and concentration which is stable over time with respect to gelling.

It is a further problem of the present invention to provide a use of a glass having an appropriate reaction speed when mixed with an acidic polymer solution, so as to allow suitable working and setting times when the glass is ground to a fine particle size.

As an additional desirable feature, hardening compositions which, when hardened, form a glass ionomer suitable for dental use, should be opaque to X-rays.

SUMMARY OF THE INVENTION

The present invention provides a hardening composition comprising
 (i) a particulate glass and
 (ii) an acidic copolymer reactive with the particulate glass under aqueous conditions, characterized in that
said particulate glass comprises
  a. 10-35% by weight of silica
  b. 10-35% by weight of alumina
  c. 3-30% by weight of zinc oxide
  d. 4-30% by weight of $P_2O_5$
  e. 3-25% by weight of fluoride, and
said acidic copolymer has a mean molecular weight, $M_w$, of from 50000 to 200000 and is obtainable by a process comprising the copolymerization of a mixture containing the following acids, or hydrolysable derivatives thereof
 (1) acrylic acid, and
 (2) an acrylic acid ester of the following formula (I):

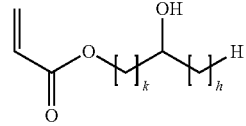

wherein k is an integer of from 1 to 5 and h is an integer from 0 to (5−k), and/or a compound of the following formula (II):

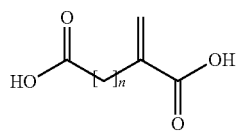

wherein n is an integer of from 1 to 3, and optionally
(3) a compound of the following formula (III):

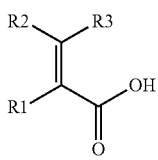

wherein R1 is hydrogen or a C1-6 alkyl group, and R2 and R3 independently represent hydrogen, a C1-6 alkyl group or a moiety of the following formula (IV):

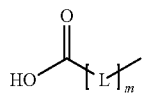

wherein m independently is an integer of from 0 to 3, and L is —$CH_2$— or —CH=CH—;
provided that at least one of R1, R2 or R3 is not hydrogen.

Furthermore, the present invention provides an aqueous polymer solution comprising 10 to 65% by weight of an acidic copolymer having a mean molecular weight, $M_w$, of from 50000 to 200000 and which is obtainable by the copolymerization of a mixture containing the following acids or hydrolysable derivatives thereof
(1) acrylic acid, and
(2) an acrylic acid ester of the following formula (I):

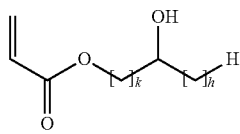

wherein k is an integer of from 1 to 5 and h is an integer from 0 to (5−k), and/or
a compound of the following formula (II):

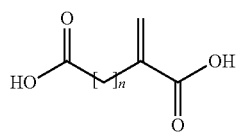

wherein n is an integer of from 1 to 3, and optionally (3) a compound of the following formula (III):

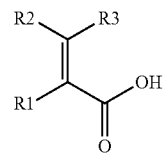

wherein R1 is hydrogen or a C1-6 alkyl group, and R2 and R3 independently represent hydrogen a C1-6 alkyl group or a moiety of the following formula (IV):

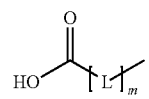

wherein m independently is an integer of from 0 to 3, and L is —$CH_2$— or —CH=CH—;
provided that at least one of R1, R2 or R3 is not hydrogen.

DETAILED DESCRIPTION OF THE INVENTION

The present invention relates to a hardening composition. The hardening composition comprises a particulate glass and an acidic copolymer reactive with the particulate glass under aqueous conditions.

The particulate glass of the present invention is a particulate reactive aluminosilicate glass composition. The composition contains silicon, aluminum, zinc, phosphorus and fluorine as essential elements. Silicon, aluminum, zinc and phosphorus are contained in the composition predominantly as oxides.

The particulate glass comprises
a. 10-35% by weight of silica
b. 10-35% by weight of alumina
c. 3-30% by weight of zinc oxide
d. 4-30% by weight of $P_2O_5$
e. 3-25% by weight of fluoride, The properties of a glass ionomer depends on many factors, but general trends can be seen between the composition of the glass and the glass ionomer properties. Since the trends are not necessarily linear and there are many interactions, trends should not be extrapolated too far from known points. A change of most components in a glass affects the degree of crosslinking in the glass, and therefore most compositional changes affect the reactivity in some way. The following trends are seen in multiple regression analysis of the glass and properties of the resulting glass ionomers.

Silica (calculated as $SiO_2$) is contained in the glass composition used according to the invention in an amount of from 10-35% by weight. In a preferred embodiment, silica is contained in an amount of from 20-25% by weight. If the amount in the composition is below the range, the solubility and reactivity of the glass may be too high, and the resulting glass ionomer may have low strength. If the amount in the composition is above the range, the properties of the glass may be deteriorated, and the resulting glass ionomer again may tend to become too fast setting.

Alumina (calculated as $Al_2O_3$) is contained in the glass composition used according to the invention in an amount of from 10-35% by weight. In a preferred embodiment, alumina is contained in an amount of from 20-25% by weight. If the amount in the composition is below the range, the properties of the glass may be deteriorated, and the glass may become very reactive. If the amount in the composition is above the range, the properties of the glass may be deteriorated, and the glass ionomer may have low strength.

The weight ratio between silica and alumina is preferably in a range of from 1.2 to 0.8, more preferably in a range of from 1.15 to 1.0. If the ratio in the composition is below the range, the properties of the glass may be deteriorated, and the glass may become very reactive. If the ratio in the composition is above the range, the properties of the glass may be deteriorated, and the reactivity of the glass may become very high and difficult to regulate.

Zinc oxide (calculated as ZnO) is contained in the glass composition used according to the invention in an amount of from 3-30% by weight. In a preferred embodiment, zinc oxide is contained in an amount of from 13-18% by weight. If the amount in the composition is below the range, the properties of the glass may be deteriorated, and the rate of release of zinc ions from the glass ionomer will decrease. If the amount in the composition is above the range, the properties of the glass may be deteriorated, and the glass may tend to become too reactive.

Phosphorus pentoxide (calculated as $P_2O_5$) is contained in the glass composition used according to the invention in an amount of from 4-30% by weight. In a preferred embodiment, phosphorus pentoxide is contained in an amount of from 14 to 18% by weight. Phosphorus atoms may also be contained in the composition in the form of a phosphate. If the amount of phosphorus pentoxide in the composition is outside this range, then the working time and setting time may be deteriorated.

Fluoride is contained in the glass composition according to the invention in an amount of from 3-25% by weight. In a preferred embodiment, fluoride is contained in an amount of from 4-7% by weight. If the amount in the composition is below this range, the properties of the glass may be deteriorated. The glass may become less reactive and the strength of a glass ionomer made from it may be reduced. If the amount in the composition is above the range, the properties of the glass are deteriorated. The glass may become highly reactive and more difficult to use in a glass ionomer formulation.

Besides the essential elements, the particulate glass composition of the present invention may further comprise from 18-21% by weight of calcium oxide plus strontium oxide.

The particulate glass composition preferably essentially does not contain any alkaline metal oxides. In particular, the glass composition contains at most 2% by weight, preferably at most 1.5% by weight, of alkaline metal oxides, $M_2O$, wherein M is Li, Na, or K. In a preferred embodiment, the content of $Na_2O$ in the particulate glass is less than 1% by weight. If the alkaline metals are present in the composition in amounts above these ranges, the glass may become more soluble and the working time and the setting time of a corresponding hardening composition may be deteriorated.

The glass composition preferably does essentially not contain any boron atoms. In particular, the composition contains at most 2% by weight, preferably at most 1.5% by weight, of $B_2O_3$. If the content of $B_2O_3$ in the composition is above this range, the hydrolytic stability of a corresponding hardening composition may be deteriorated.

In a preferred embodiment, the glass composition is characterized by a weight ratio of zinc oxide to $P_2O_5$ of from 2.0 to 0.2. If the weight ratio is outside this range, the working time and the setting time of a corresponding hardening composition and/or the mechanical properties of a corresponding glass ionomer may be deteriorated.

In a further preferred embodiment, the glass composition is characterized by a weight ratio of the sum of zinc oxide and strontium oxide to silica of from 1.0 to 1.95, more preferably from 1.25 to 1.6. If the weight ratio is outside this range, the working time and the setting time of a corresponding hardening composition and/or the mechanical properties of a corresponding glass ionomer may be deteriorated.

In a further preferred embodiment, the glass composition is characterized by a weight ratio of the sum of zinc oxide and fluoride to $P_2O_5$ of from 0.8 to 3.0. If the weight ratio is outside this range, the working time and the setting time of a corresponding hardening composition and/or the mechanical properties of a corresponding glass ionomer may be deteriorated.

The aluminosilicate glass composition of the invention may be prepared according to any method for preparing a dental glass. In particular, it is possible to prepare a mixture of suitable starting materials. Accordingly, the mixture may typically contain silica, aluminum oxide, phosphorus pentoxide, and a suitable fluoride source such as aluminum trifluoride or $Na_3AlF_6$. Optionally, the mixture may contain calcium or strontium carbonate or the corresponding fluorides ($CaF_2$ or $SrF_2$). Advantageously, the mixture is subsequently shaken to thoroughly mix the components together. Subsequently, the mixture heated at a suitable rate of 5.0 to 300° C./min to a first elevated temperature of about 600 to 800° C. to allow degassing and moisture loss. After a suitable amount of time at the elevated temperature, the mixture is heated at a suitable rate of 50 to 300° C./min to a second elevated temperature of about 1300 to 1500° C. and held at this temperature for about 60 to 180 minutes, then the temperature is increased at a suitable rate of 50 to 300° C./min to a third elevated temperature of from 1400 to 1600° C. and held at this temperature for about 10 to 60 minutes. After withdrawing the crucible from the oven, the molten glass is poured directly into cold water to give broken glass fragments.

The glass fragments may then be milled, for example in a dry ball mill, to give a powder with a mean particle size in a range of less than 100 μm, preferably less than 10 μm. This powder may then be further milled, for example in water slurry, to give glass powder with an even smaller mean particle size, typically in the range of from 0.1 to 8 μm. Preferably, the particulate glass filler has a mean particle size in the range of from 0.1 to 100 μm, more preferably in the range of from 0.5 to 25 μm, most preferably in the range of from 1.0 to 3.5 μm. Because the reactivity of the glass particles depends on their size and surface area, it is important that the mean particle size is carefully controlled.

Particle size measurements may be made by any conventional method such as embodied by a Malvern Particle Master Sizer model S.

The glass composition used according to the invention may be used for the preparation of a dental restorative composition.

The particulate glass filler is incorporated into a hardening composition according to the present invention which further comprises an acidic copolymer reactive with the particulate glass under aqueous conditions.

The acidic copolymer used in the hardening composition of the invention has a mean molecular weight, $M_w$, of from 50000 to 200000, preferably between 75000 and 150000, more preferably between 100000 and 130000. Alternatively, the acidic copolymer used in the hardening composition of the invention has a mean molecular weight, $M_n$ of from 5000 to 40000, preferably between 10000 and 30000, more preferably between 15000 and 25000. If the mean molecular weights, $M_n$ and $M_w$, are too low, the acidic copolymer does not provide the required mechanical properties to the final glass ionomer. If the mean molecular weights, $M_n$ and $M_w$, are too high, the polymer solution and glass ionomer powder become hard to mix since the viscosity of the polymer solutions increases with increase in molecular weight.

The mean molecular weights, $M_n$ and $M_w$, and molecular weight distributions of the acidic copolymers disclosed herein were determined using the gel permeation chromatography (GPC) analysis method described below and in further detail in the Experimental part 4. The GPC analysis method described herein uses an aqueous solution (11.88 g/L $Na_2HPO_4$ in deionised water) as the eluant (eluting agent). The combination of columns containing the solid support (permeation gel) which was used for GPC analysis comprised a precolumn (PSS Suprema, 10 μm, 30 Å, ID 8 mm×50 mm) and two further columns (PSS Suprema, 10 μm, 30 Å and 1000 Å, ID 8 mm×300 mm). Injection of 50 μL of a given acidic copolymer sample in a concentration of 3.0 g/L was performed prior to elution at 23° C. using a flow rate of 1.0 mL/min. The eluted acidic copolymers were detected using ultraviolet light (UV) at 230 nm or by using a differential refractometer, so as to produce GPC analysis elution profile results for each sample. Sodium polyacrylate standards were analyzed using the same methodology in order to generate a calibration curve for the column combination. The mean molecular weight, $M_n$ and $M_w$, and molecular weight distribution of the samples of acidic copolymers were calculated by computer integration of their elution profile results, based on the sodium polyacrylate calibration curve.

The acid copolymer is obtainable by a process comprising the copolymerization of a mixture containing acrylic acid, and an acrylic acid ester of (I)

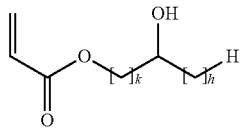

wherein k is an integer of from 1 to 5 and h is an integer from 0 to (5−k).

The acid copolymer is alternatively obtainable by a process comprising the copolymerization of a mixture containing acrylic acid, a compound of (II)

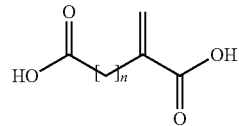

wherein n is an integer of from 1 to 3.

The acid copolymer is alternatively obtainable by a process comprising the copolymerization of a mixture containing acrylic acid, an acrylic acid ester of (I) and a compound of (II).

The mixtures may optionally further contain a compound of the following formula (III):

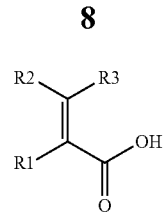

In formula (III), R1 is hydrogen or a linear, branched or cyclic C1-6 alkyl group such as methyl-, ethyl-, propyl-, isopropyl-, n-butyl-, (R)-sec-butyl-, (S)-sec-butyl-, sec-butyl-, isobutyl-, tert-butyl-, n-pentyl-, (R)-2-pentyl-, (S)-2-pentyl-, 2-pentyl-, 3-pentyl-, 2-methyl-butyl-, isopentyl-, (R)-3-methyl-2-butyl-, (S)-3-methyl-2-butyl-, 3-methyl-2-butyl-, tert-pentyl-, 2,2-dimethyl-propyl-, n-hexyl-, (R)-2-hexyl-, (S)-2-hexyl-, 2-hexyl-, (R)-3-hexyl-, (S)-3-hexyl-, 3-hexyl-, 2-methyl-pentyl-, 2-methyl-2-pentyl-, (R)-2-methyl-3-pentyl-, (S)-2-methyl-3-pentyl-, 2-methyl-3-pentyl-, (R)-4-methyl-2-pentyl-, (S)-4-methyl-2-pentyl-, 4-methyl-2-pentyl-, 4-methyl-pentyl-, 3-methyl-pentyl-, (2R,3R)-3-methyl-2-pentyl-, (2R,3S)-3-methyl-2-pentyl-, (2S,3R)-3-methyl-2-pentyl-, (2S,3S)-3-methyl-2-pentyl-, 3-methyl-2-pentyl-, 3-methyl-3-pentyl-, 2-ethyl-butyl-, 2,3-dimethyl-butyl-, 2,3-dimethyl-2-butyl-, 2,2-dimethyl-butyl-, (R)-3,3-dimethyl-2-butyl-, (S)-3,3-dimethyl-2-butyl-, 3,3-dimethyl-2-butyl-, 3,3-dimethyl-butyl-, cyclopropyl-, 1-methyl cyclopropyl-, (1R,2R)-2-methyl cyclopropyl-, (1R,2S)-2-methyl cyclopropyl-, (1S,2R)-2-methyl cyclopropyl-, (1S,2S)-2-methyl cyclopropyl-, 2-methyl cyclopropyl-, 1-ethyl cyclopropyl-, (1R,2R)-2-ethyl cyclopropyl-, (1R,2S)-2-ethyl cyclopropyl-, (1S,2R)-2-ethyl cyclopropyl-, (1S,2S)-2-ethyl cyclopropyl-, 2-ethyl cyclopropyl-, 1-propyl cyclopropyl-, (1R,2R)-2-propyl cyclopropyl-, (1R,2S)-2-propyl cyclopropyl-, (1S,2R)-2-propyl cyclopropyl-, (1S,2S)-2-propyl cyclopropyl-, 2-propyl cyclopropyl-, (1R,2R)-1,2-dimethyl cyclopropyl-, (1R,2S)-1,2-dimethyl cyclopropyl-, (1S,2R)-1,2-dimethyl cyclopropyl-, (1S,2S)-1,2-dimethyl cyclopropyl-, 1,2-dimethyl cyclopropyl-, (R)-2,2-dimethyl cyclopropyl-, (S)-2,2-dimethyl cyclopropyl-, 2,2-dimethyl cyclopropyl-, (2R,3R)-2,3-dimethyl cyclopropyl-, (2R,3S)-2,3-dimethyl cyclopropyl-, (2S,3R)-2,3-dimethyl cyclopropyl-, (2S,3S)-2,3-dimethyl cyclopropyl-, 2,3-dimethyl cyclopropyl-, (2R,3R)-1,2,3-trimethyl cyclopropyl-, (2R,3S)-1,2,3-trimethyl cyclopropyl-, (2S,3R)-1,2,3-trimethyl cyclopropyl-, (2S,3S)-1,2,3-trimethyl cyclopropyl-, 1,2,3-trimethyl cyclopropyl-, (R)-1,2,2-trimethyl cyclopropyl-, (S)-1,2,2-trimethyl cyclopropyl-, 1,2,2-trimethyl cyclopropyl-, (1R,3R)-2,2,3-trimethyl cyclopropyl-, (1R,3S)-2,2,3-trimethyl cyclopropyl-, (1S,3R)-2,2,3-trimethyl cyclopropyl-, (1S,3S)-2,2,3-trimethyl cyclopropyl-, 2,2,3-trimethyl cyclopropyl-, (1R,2R)-1-ethyl-2-methyl cyclopropyl-, (1R,2S)-1-ethyl-2-methyl cyclopropyl-, (1S,2R)-1-ethyl-2-methyl cyclopropyl-, (1S,2S)-1-ethyl-2-methyl cyclopropyl-, 1-ethyl-2-methyl cyclopropyl-, (1R,2R)-2-ethyl-1-methyl cyclopropyl-, (1R,2S)-2-ethyl-1-methyl cyclopropyl-, (1S,2R)-2-ethyl-1-methyl cyclopropyl-, (1S,2S)-2-ethyl-1-methyl cyclopropyl-, 2-ethyl-1-methyl cyclopropyl-, (1R,2R)-2-ethyl-2-methyl cyclopropyl-, (1R,2S)-2-ethyl-2-methyl cyclopropyl-, (1S,2R)-2-ethyl-2-methyl cyclopropyl-, (1S,2S)-2-ethyl-2-methyl cyclopropyl-, 2-ethyl-2-methyl cyclopropyl-, (1R,2R,3R)-2-ethyl-3-methyl cyclopropyl-, (1R,2R,3S)-2-ethyl-3-methyl cyclopropyl-, (1R,2S,3R)-2-ethyl-3-methyl cyclopropyl-, (1S,2R,3R)-2-ethyl-3-methyl cyclopropyl-, (1R,2S,3S)-2-ethyl-3-methyl cyclopropyl-, (1S,2R,3S)-2-ethyl-3-methyl cyclopropyl-, (1S,2S,3R)-2-ethyl-3-methyl cyclopropyl-, (1S,2S,3S)-2-ethyl-3-methyl cyclopropyl-, 2-ethyl-3-methyl cyclopropyl-, cyclobutyl-, 1-methyl cyclobutyl-, (1R,2R)-2-methyl cyclobutyl-, (1R,2S)-2-methyl cyclobutyl-, (1S,2R)-2-methyl cyclobutyl-, (1S,2S)-2-methyl cyclobutyl-, 2-methyl cyclobutyl-, 3-methyl, cyclobutyl-,1-ethyl cyclobutyl-, (1R,2R)-2-ethyl cyclobutyl-, (1R, 2S)-2-ethyl cyclobutyl-, (1S,2R)-2-ethyl cyclobutyl-, (1S, 2S)-2-ethyl cyclobutyl-, 2-ethyl cyclobutyl-, 3-ethyl cyclobutyl-, (1R,2R)-1,2-dimethyl cyclobutyl-, (1R,2S)-1,2-dimethyl cyclobutyl-, (1S,2R)-1,2-dimethyl cyclobutyl-, (1S, 2S)-1,2-dimethyl cyclobutyl-, 1,2-dimethyl cyclobutyl-, 1,3-dimethyl cyclobutyl-, (R)-2,2-dimethyl cyclobutyl-, (S)-2,2-dimethyl cyclobutyl-, 2,2-dimethyl cyclobutyl-, (1R,2R,3R)-2,3-dimethyl cyclobutyl-, (1R,2R,3S)-2,3-dimethyl cyclobutyl-, (1R,2S,3R)-2,3-dimethyl cyclobutyl-, (1S,2R, 3R)-2,3-dimethyl cyclobutyl-, (1R,2S,3S)-2,3-dimethyl cyclobutyl-, (1S,2S,3R)-2,3-dimethyl cyclobutyl-, (1S,2R, 3S)-2,3-dimethyl cyclobutyl-, (1S,2S,3S)-2,3-dimethyl cyclobutyl-, 2,3-dimethyl cyclobutyl-, (1R,2R)-2,4-dimethyl cyclobutyl-, (1R,2S)-2,4-dimethyl cyclobutyl-, (1S,2R)-2,4-dimethyl cyclobutyl-, (1S,2S)-2,4-dimethyl cyclobutyl-, 2,4-dimethyl cyclobutyl-, 3,3-dimethyl cyclobutyl-, cyclopentyl-, 1-methyl cyclopentyl-, (1R,2R)-2-methyl cyclopentyl-, (1R,2S)-2-methyl cyclopentyl-, (1S,2R)-2-methyl cyclopentyl-, (1S,2S)-2-methyl cyclopentyl-, 2-methyl cyclopentyl-, (1R,2R)-3-methyl cyclopentyl-, (1R,2S)-3-methyl cyclopentyl-, (1S,2R)-3-methyl cyclopentyl-, (1S,2S)-3-methyl cyclopentyl-, 3-methyl cyclopentyl- or cyclohexyl-.

In formula (III), R2 and R3 independently represent hydrogen, a linear, branched or cyclic C1-6 alkyl group such as methyl-, ethyl-, propyl-, isopropyl-, n-butyl-, (R)-sec-butyl-, (S)-sec-butyl-, sec-butyl-, isobutyl-, tert-butyl-, n-pentyl-, (R)-2-pentyl-, (S)-2-pentyl-, 2-pentyl-, 3-pentyl-, 2-methyl-butyl-, isopentyl-, (R)-3-methyl-2-butyl-, (S)-3-methyl-2-butyl-, 3-methyl-2-butyl-, tert-pentyl-, 2,2-dimethyl-propyl-, n-hexyl-, (R)-2-hexyl-, (S)-2-hexyl-, 2-hexyl-, (R)-3-hexyl-, (S)-3-hexyl-, 3-hexyl-, 2-methyl-pentyl-, 2-methyl-2-pentyl-, (R)-2-methyl-3-pentyl-, (S)-2-methyl-3-pentyl-, 2-methyl-3-pentyl-, (R)-4-methyl-2-pentyl-, (S)-4-methyl-2-pentyl-, 4-methyl-2-pentyl-, 4-methyl-pentyl-, 3-methyl-pentyl-, (R)-3-methyl-2-pentyl-, (S)-3-methyl-2-pentyl-, 3-methyl-2-pentyl-, 3-methyl-3-pentyl-, 2-ethyl-butyl-, 2,3-dimethyl-butyl-, 2,3-dimethyl-2-butyl-, 2,2-dimethyl-butyl-, (R)-3,3-dimethyl-2-butyl-, (S)-3,3-dimethyl-2-butyl-, 3,3-dimethyl-2-butyl-, 3,3-dimethyl-butyl-, cyclopropyl-, 1-methyl cyclopropyl-, (1R,2R)-2-methyl cyclopropyl-, (1R,2S)-2-methyl cyclopropyl-, (1S,2R)-2-methyl cyclopropyl-, (1S, 2S)-2-methyl cyclopropyl-, 2-methyl cyclopropyl-, 1-ethyl cyclopropyl-, (1R,2R)-2-ethyl cyclopropyl-, (1R,2S)-2-ethyl cyclopropyl-, (1 S,2R)-2-ethyl cyclopropyl-, (1S,2S)-2-ethyl cyclopropyl-, 2-ethyl cyclopropyl-, 1-propyl cyclopropyl-, (1R,2R)-2-propyl cyclopropyl-, (1R,2S)-2-propyl cyclopropyl-, (1 S,2R)-2-propyl cyclopropyl-, (1S,2S)-2-propyl cyclopropyl-, 2-propyl cyclopropyl-, (1R,2R)-1,2-dimethyl cyclopropyl-, (1R,2S)-1,2-dimethyl cyclopropyl-, (1S,2R)-1,2-dimethyl cyclopropyl-, (1S,2S)-1,2-dimethyl cyclopropyl-, 1,2-dimethyl cyclopropyl-, (R)-2,2-dimethyl cyclopropyl-, (S)-2,2-dimethyl cyclopropyl-, 2,2-dimethyl cyclopropyl-, (2R,3R)-2,3-dimethyl cyclopropyl-, (2R,3S)-2,3-dimethyl cyclopropyl-, (2S,3R)-2,3-dimethyl cyclopropyl-, (2S,3S)-2,3-dimethyl cyclopropyl-, 2,3-dimethyl cyclopropyl-, (2R,3R)-1,2,3-trimethyl cyclopropyl-, (2R,3S)-1,2,3-trimethyl cyclopropyl-, (2S,3R)-1,2,3-trimethyl cyclopropyl-, (2S,3S)-1,2,3-trimethyl cyclopropyl-, 1,2,3-trimethyl cyclopropyl-, (R)-1,2,2-trimethyl cyclopropyl-, (8)-1,2,2-trimethyl cyclopropyl-, 1,2,2-trimethyl cyclopropyl-, (1R,3R)-2,2,3-trimethyl cyclopropyl-, (1R,3S)-2,2,3-trimethyl cyclopropyl (1S, 3R)-2,2,3-trimethyl cyclopropyl-, (1S,3S)-2,2,3-trimethyl cyclopropyl-, 2,2,3-trimethyl cyclopropyl-, (1R,2R)-1-ethyl-2-methyl cyclopropyl-, (1R,2S)-1-ethyl-2-methyl cyclopropyl-, (1S,2R)-1-ethyl-2-methyl cyclopropyl-, (1S,2S)-1-ethyl-2-methyl cyclopropyl-, 1-ethyl-2-methyl cyclopropyl-, (1R,2R)-2-ethyl-1-methyl cyclopropyl-, (1R,2S)-2-ethyl-1-methyl cyclopropyl-, (1S,2R)-2-ethyl-1-methyl cyclopropyl-, (1S,2S)-2-ethyl-1-methyl cyclopropyl-, 2-ethyl-1-methyl cyclopropyl-, (1R,2R)-2-ethyl-2-methyl cyclopropyl-, (1R,2S)-2-ethyl-2-methyl cyclopropyl-, (1S,2R)-2-ethyl-2-methyl cyclopropyl-, (1S,2S)-2-ethyl-2-methyl cyclopropyl-, 2-ethyl-2-methyl cyclopropyl-, (1R,2R,3R)-2-ethyl-3-methyl cyclopropyl-, (1R,2R,3S)-2-ethyl-3-methyl cyclopropyl-, (1R,2S,3R)-2-ethyl-3-methyl cyclopropyl-, (1S,2R,3R)-2-ethyl-3-methyl cyclopropyl-, (1R,2S,3S)-2-ethyl-3-methyl cyclopropyl-, (1S,2R,3S)-2-ethyl-3-methyl cyclopropyl-, (1S,2S,3R)-2-ethyl-3-methyl cyclopropyl-, (1S,2S,3S)-2-ethyl-3-methyl cyclopropyl-, 2-ethyl-3-methyl cyclopropyl-, cyclobutyl-, 1-methyl cyclobutyl-, (1R,2R)-2-methyl cyclobutyl-, (1R,2S)-2-methyl cyclobutyl-, (1S,2R)-2-methyl cyclobutyl-, (1S,2S)-2-methyl cyclobutyl-, 2-methyl cyclobutyl-, 3-methyl cyclobutyl-,1-ethyl cyclobutyl-, (1R,2R)-2-ethyl cyclobutyl-, (1R,2S)-2-ethyl cyclobutyl-, (1S,2R)-2-ethyl cyclobutyl-, (1S,2S)-2-ethyl cyclobutyl-, 2-ethyl cyclobutyl-, 3-ethyl cyclobutyl-, (1R,2R)-1,2-dimethyl cyclobutyl-, (1R,2S)-1,2-dimethyl cyclobutyl-, (1S, 2R)-1,2-dimethyl cyclobutyl-, (1S,2S)-1,2-dimethyl cyclobutyl-, 1,2-dimethyl cyclobutyl-, 1,3-dimethyl cyclobutyl-, (R)-2,2-dimethyl cyclobutyl-, (S)-2,2-dimethyl cyclobutyl-, 2,2-dimethyl cyclobutyl-, (1R,2R,3R)-2,3-dimethyl cyclobutyl-, (1R,2R,3S)-2,3-dimethyl cyclobutyl-, (1R,2S, 3R)-2,3-dimethyl cyclobutyl-, (1S,2R,3R)-2,3-dimethyl cyclobutyl-, (1R,2S,3S)-2,3-dimethyl cyclobutyl-, (1S,2S, 3R)-2,3-dimethyl cyclobutyl-, (1S,2R,3S)-2,3-dimethyl cyclobutyl-, (1S,2S,3S)-2,3-dimethyl cyclobutyl-, 2,3-dimethyl cyclobutyl-, (1R,2R)-2,4-dimethyl cyclobutyl-, (1R, 2S)-2,4-dimethyl cyclobutyl-, (1S,2R)-2,4-dimethyl cyclobutyl-, (1R,2S)-2,4-dimethyl cyclobutyl-, 2,4-dimethyl cyclobutyl-, 3,3-dimethyl cyclobutyl-, cyclopentyl-, 1-methyl cyclopentyl-, (1R,2R)-2-methyl cyclopentyl-, (1R,2S)-2-methyl cyclopentyl-, (1S,2R)-2-methyl cyclopentyl-, (1S, 2S)-2-methyl cyclopentyl-, 2-methyl cyclopentyl-, (1R,2R)-3-methyl cyclopentyl-, (1R,2S)-3-methyl cyclopentyl-, (1S, 2R)-3-methyl cyclopentyl-, (1S,2S)-3-methyl cyclopentyl-, 3-methyl cyclopentyl- or cyclohexyl-, or a moiety of the following formula (IV):

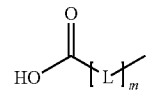

wherein m independently is an integer of from 0 to 3, and L is —CH$_2$— or —CH=CH—. In a compound of formula (III), that at least one of R1, R2 or R3 is not hydrogen.

The mixture may also contain an acidic polymerizable monomer having a moiety selected from a phosphonate group or a sulfohate group.

Preferred examples of compounds of formula (I) include, but are not restricted to 2-hydroxyethyl acrylic acid ester (ethylene glycol monoacrylate), (R)-2-hydroxypropyl acrylic acid ester, (S)-2-hydroxypropyl acrylic acid ester, 2-hydroxypropyl acrylic acid ester, 3-hydroxypropyl acrylic acid ester, (R)-2-hydroxybutyl acrylic acid ester, (S)-2-hydroxybutyl acrylic acid ester, 2-hydroxybutyl acrylic acid ester, (R)-3-hydroxybutyl acrylic acid ester, (S)-3-hydroxybutyl acrylic acid ester, 3-hydroxybutyl acrylic acid ester, 4-hydroxybutyl acrylic acid ester, (R)-2-hydroxypentyl acrylic acid ester, (S)-2-hydroxypentyl acrylic acid ester, 2-hydroxypentyl acrylic acid ester, (R)-3-hydroxypentyl acrylic acid ester, (S)-3-hydroxypentyl acrylic acid ester, 3-hydroxypentyl acrylic acid ester, (R)-4-hydroxypentyl acrylic acid ester, (S)-4-hydroxypentyl acrylic acid ester, 4-hydroxypentyl acrylic acid ester, 5-hydroxypentyl acrylic acid ester, (R)-2-hydroxyhexyl acrylic acid ester, (S)-2-hydroxyhexyl acrylic acid ester, 2-hydroxyhexyl acrylic acid ester, (R)-3-hydroxyhexyl acrylic acid ester, (S)-3-hydroxyhexyl acrylic acid ester, 3-hydroxyhexyl acrylic acid ester, (R)-4-hydroxyhexyl acrylic acid ester, (S)-4-hydroxyhexyl acrylic acid ester, 4-hydroxyhexyl acrylic acid ester, (R)-5-hydroxyhexyl acrylic acid ester, (S)-5-hydroxyhexyl acrylic acid ester, 5-hydroxyhexyl acrylic acid ester or 6-hydroxyhexyl acrylic acid ester, either singly or in combination.

Preferred examples of compounds of formula (II) include, but are not restricted to itaconic acid (also known as 2-methylene butanedioic acid), 2-methylene pentanedioic acid or 2-methylene hexanedioic acid, either singly or in combination.

Preferred examples of a compound of the formula (III) include, but are not restricted to, cis-aconitic acid, trans-aconitic acid, angelic acid, cis-citraconic acid, trans-citraconic acid, cis-crotonic acid, trans-crotonic acid, fumaric acid, cis-glutaconic acid, trans-glutaconic acid, maleic acid, cis-mesaconic acid, trans-mesaconic acid, methacrylic acid, cis,cis-muconic acid, cis,trans-muconic acid, trans,trans-muconic acid, tiglic acid, vinyl phosphonic acid, vinyl phosphonate (wherein the phosphonate may be present as the sodium or potassium salt), vinyl sulfonic acid or vinyl sulfonate (wherein the sulfonate may be present as the sodium or potassium salt), either singly or in combination.

Most preferred are acidic copolymers obtainable by a process comprising the copolymerization of a mixture containing acrylic acid and itaconic acid as the monomers.

In a preferred embodiment, the components making up the composition to be polymerized into the acidic copolymer are characterized by a weight ratio of acrylic acid/itaconic acid between 99/1 and 80/20, more preferably in a ratio of between 98/2 and 85/15. If the weight ratio is too low, the resulting acidic copolymer cannot be formed within the range of mean molecular weights disclosed by the invention, or the polyacid solution formed by dissolving the resulting acidic copolymer in water cannot be produced in the concentrations necessary for the invention, as disclosed. If the weight ratio is too high (i.e. a polymer of acrylic acid is used), the solution formed by dissolving the resulting acidic polymer in water is not physically stable and may gel over time.

In a preferred embodiment, the acidic copolymers of the invention may alternatively be formed in a two-step process, whereby appropriate monomers are first copolymerised to form an acidic copolymer precursor which is then hydrolysed to form the acidic copolymers of the present invention.

By way of example, acrylic acid anhydride can be used as a hydrolysable derivative of acrylic acid and itaconic acid anhydride can be used as a hydrolysable derivative of itaconic acid. Upon copolymerisation of these monomers, the corresponding anhydride copolymer is formed which, upon subsequent hydrolysis, forms a mixed acrylic acid-itaconic acid copolymer, according to the invention.

In the above example, both acidic monomeric components are "masked" as the anhydrides, but acidic copolymer precursors which are susceptible to hydrolysis are also formed when a minimum of one of the monomeric components is "masked" as the anhydride. Furthermore, any monomer which yields acrylic acid or an alkenoic acid upon hydrolysis may be used in this two-step process for formation of an acidic copolymer, provided that the acidic copolymer precursor is comprised of (1) acrylic acid, and
(2) an acrylic acid ester of the following formula (I):

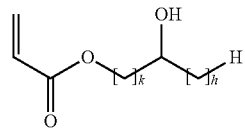

wherein k is an integer of from 1 to 5 and h is an integer from 0 to (5−k), and/or
a compound of the following formula (II):

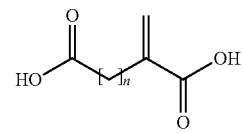

wherein n is an integer of from 1 to 3, and optionally
(3) a compound of the following formula (III):

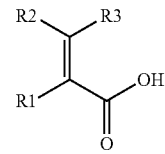

wherein R1 is hydrogen or a C1-6 alkyl group, and R2 and R3 independently represent hydrogen, a C1-6 alkyl group or a moiety of the following formula (IV):

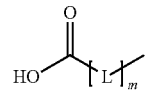

wherein m independently is an integer of from 0 to 3, and L is —CH$_2$— or —CH═CH—;
provided that at least one of R1,R2 or R3 is not hydrogen,
(as defined above), wherein at least one of (i) acrylic acid, or (ii) a compound of the formula (I) or a compound of the formula (II), or (iii) a compound of the formula (III) is replaced by one or more hydrolysable derivatives.

The hydrolysable derivatives of acrylic acid may be selected from a list which includes, but is not restricted to acrylonitrile, acrylamide, acrylic acid anhydride, acrylic acid esters [such as compounds of the formula (I)] and mixed carboxylic acid-acrylic acid anhydrides (such as acetic acid-acrylic acid anhydride), either singly or in combination.

The hydrolysable derivatives of a compound of the formula (I) of the acidic copolymer precursor may be selected from a list which includes, but is not restricted to, hydroxyl-protected derivatives. Selected examples thereof include, but are not restricted to, the triflic acid acrylic acid diester of ethylene glycol and the trialkylsilyl ethers of 2-hydroxyethyl acrylic acid ester, which may be used either singly or in combination.

Acidic copolymer precursors formed solely from hydrolysable derivatives of a compound of the formula (I) and acrylic acid (or hydrolysable derivatives thereof), will only afford the acidic copolymers of the present invention if the hydroxyalkyl acrylic acid ester moieties remain intact upon hydrolysis. This condition need not be met for those copolymer precursors which are formed from mixtures comprised of compounds (II) or (III) in addition to the above two components.

The hydrolysable derivatives of a compound of the formula (II) of the acidic copolymer precursor may be selected from a list which includes, but is not restricted to, anhydride, mixed anhydride, amide and nitrile derivatives. The derivatives are of itaconic acid, 2-methylene pentanedioic acid or 2-methylene hexanedioic acid, and may be used either singly or in combination. Selected examples thereof include, but are not restricted to, itaconic acid anhydride, itaconic amide and acetic acid-itaconic acid anhydride, which may be used either singly or in combination.

The hydrolysable derivatives of the optional component (III) of the acidic copolymer precursor may be selected from a list which includes, but is not restricted to, anhydride, mixed anhydride, amide and nitrile derivatives. The derivatives are of cis-aconitic acid, trans-aconitic acid, angelic acid, cis-citraconic acid, trans-citraconic acid, cis-crotonic acid, trans-crotonic acid, fumaric acid, cis-glutaconic acid, trans-glutaconic acid, maleic acid, cis-mesaconic acid, trans-mesaconic acid, methacrylic acid, cis,cis-muconic acid, cis,trans-muconic acid, trans,trans-muconic acid, tiglic acid, either singly or in combination.

Most preferred are acidic copolymer precursors which are formed by polymerising (i) acrylic acid anhydride and itaconic acid anhydride, or (ii) acrylonitrile and itaconic acid anhydride, or (iii) acrylic acid and itaconic acid anhydride. These acidic copolymer precursors form the acidic copolymers of the present invention upon hydrolysis.

In a preferred embodiment, the components making up the composition to be polymerized into the acidic copolymer precursor are characterized by a weight ratio of hydrolysable derivative of acrylic acid/hydrolysable derivative of itaconic acid between 99/1 and 80/20, more preferably in a ratio of between 98/2 and 85/15. If the weight ratio is too low, the acidic copolymer generated upon hydrolysis cannot be formed within the range of mean molecular weights disclosed by the invention, or cannot form solutions in the concentrations necessary for the invention, as disclosed. If the weight ratio is too high (i.e. a polymer of a hydrolysable derivative of acrylic acid is used), the solution formed by dissolving the acidic polymer generated upon hydrolysis in water is not physically stable and may gel over time.

The process by which the acidic copolymers and/or acidic copolymer precursors may be obtained involves the copolymerization of a mixture, preferably by free-radical polymerization in bulk, in solution, in an emulsion or interfacially. Polymerisation may be performed as chain-growth or step-growth polymerisation in batch or semibatch (continuous emulsion or monomer feed) processes. Polymerisation is generally performed at temperatures between 0 and 110° C. under an atmosphere of an inert gas such as nitrogen or argon, so as to exclude oxygen from the system. Polymerisation may optionally be performed in the presence of additives which may include, but are not restricted to, an emulsifier, an initiator, a catalyst, a modifier or light, or a combination thereof.

The solvents used during polymerisation may be selected from a list which includes, but is not restricted to water, acetone, methanol, ethanol, propanol, isopropanol, n-butanol, isobutanol, sec-butanol, tert-butanol, benzene, toluene, xylene, carbon tetrachloride, chloroform, tetrahydrofuran, dimethylformamide, diethyl ether, hexane, cyclohexane, ethyl acetate, butyl acetate, methyl ethyl ketone or methyl isobutyl ketone, either singly or in combination.

The emulsifier, when used, may be selected from a list which includes, but is not restricted to (i) anionic emulsifiers such as sodium, potassium or ammonium salts of fatty acids and sulfonic acids, (ii) nonionic emulsifiers such as ethoxylated fatty alcohols and alkyl phenols, and (iii) cationic emulsifiers, either singly or in combination.

The initiator may be selected from a list which includes, but is not restricted to (i) soluble peroxo compounds such as hydrogen peroxide, benzoylperoxide, methyl ethyl ketone, methyl hydroperoxide, di-tert-butyl peroxide, peracetic acid, potassium persulfate, ammonium persulfate and alkyl persulfates, (ii) soluble azo compounds such as 2,2'-azobis(isobutyronitrile), and (iii) iron(II) sulfate, sodium bisulfite, sodium thiosulfate and sodium formaldehyde sulfoxylate, either singly or in combination. Polymerisation may also be initiated with light at wavelengths of less than 360 nm or with gamma-radiation.

The catalyst may be selected from a list of iron(II) salts which includes, but is not restricted to iron(II) chloride, iron (II) bromide, iron(II) sulfate and iron(II) acetate, either singly or in combination.

The modifier may be selected from a list which includes, but is not restricted to (i) halogen-containing compounds such as carbon tetrachloride, carbon tetrabromide, bromoform, chloroform, benzyl bromide and bromotrichloromethane, (ii) thiols such as butylthiol and dodecylthiol, and (iii) branched alcohols such as 2-propanol, (R)-2-butanol, (S)-2-butanol, isobutanol, t-butanol, (R)-2-pentanol, (S)-2-pentanol, 3-pentanol, isopentanol, (R)-3-methyl-2-butanol, (S)-3-methyl-2-butanol, 2-methyl-butanol, 2-methyl-2-butanol, 2,2-dimethyl-propanol, (R)-2-hexanol, (S)-2-hexanol, (R)-3-hexanol, (S)-3-hexanol, 2-methyl-pentanol, 2-methyl-2-pentanol, (R)-2-methyl-3-pentanol-, (S)-2-methyl-3-pentanol-,(R)-4-methyl-2-pentanol, (S)-4-methyl-2-pentanol, 4-methyl-pentanol, 3-methyl-pentanol, (R)-3-methyl-2-pentanol, (S)-3-methyl-2-pentanol, 3-methyl-3-pentanol, 2-ethyl-butanol, 2,3-dimethyl-butanol, 2,3-dimethyl-2-butanol, 2,2-dimethyl-butanol, (R)-3,3-dimethyl-2-butanol, (S)-3,3-dimethyl-2-butanol and 3,3-dimethyl-butanol, either singly or in combination.

The process by which the acidic copolymers are obtained may optionally include the removal of heat to control the kinetics of polymerisation and/or elimination of residual monomers from the copolymer after polymerisation is complete. The elimination of monomers may include, but is not restricted to, the methods of (i) removal under heat, if necessary with the application of reduced pressure and/or the addition of antifoaming agents, or (ii) continuous removal by applying a vacuum to the polymer dispersion and blowing steam into it.

In the case of acidic copolymers which are formed in a two-step process via an acidic copolymer precursor, an additional hydrolysis step is required. Hydrolysis of the acidic copolymer precursor can be effected in water or in mixed solvent systems including, but not limited to, water and tetrahydrofuran, water and methanol, water and ethanol, water and isopropanol, and water and butanol. The aqueous solutions may contain an inorganic salt, including, but not restricted to sodium hydroxide, lithium hydroxide, potassium hydroxide, sodium carbonate and ammonium hydroxide.

The acidic copolymers obtained according to the present invention can be employed as coating materials, adhesives, fibre-treating agents and impregnants to give products which have desirable physical and chemical properties. In particular, the acidic copolymers are used in the formation of hardening compositions according to the present invention.

The method of producing a hardening composition which may be hardened to form a cross-linked glass ionomer comprises the reaction of the particulate glass with the acidic copolymer in the presence of water.

According to the present invention, the process for the preparation of a hardening composition comprises the following steps:
(a) providing a component containing an acidic copolymer;
(b) providing a component containing a particulate glass;
(c) mixing components of step (a) and (b) in the presence of water for preparing a hardening composition.

The hardening compositions for forming a glass ionomer may be provided as two-part packs, one part comprising an aqueous solution of the acidic copolymer (and, optionally, the setting retarder and/or pigment) and the other part comprising the particulate glass, so that when the packs are combined, a hardening composition according to the invention is formed.

In a preferred embodiment, a dry blend or admixture (also known as a water settable glass ionomer) may alternatively be formed from particulate glass and the acidic copolymer in anhydrous form (preferably as a powder), preferably wherein the said particulate glass is provided mixed with the said acidic copolymer in anhydrous form. This anhydrous mixture (formed, for example, by freeze-drying of each component prior to mixing) requires subsequent addition of water to form a composition which will subsequently harden to form a glass ionomer. In this case setting retarders and/or pigments may be present in the dry blend or in the water. Furthermore, the stability of the polymer in solution is, therefore, not important, but the optimized molecular weight range of the acidic copolymer and the composition of the particulate glass, as claimed in this invention, are still advantageous.

In a further alternative, one part comprising an aqueous solution of the acidic copolymer (and, optionally, the setting retarder and/or pigment) and the other part comprising a dry blend of particulate glass and acidic copolymer may be provided to form a cement-forming composition. In this case, the setting retarders and/or pigments may be present in the dry blend or in the aqueous solution of acidic copolymer.

In a preferred embodiment, the mixing of the powder and liquid systems described above may be performed by hand. Mixing is, however, not restricted to manual methods, but may also be performed mechanically.

The powder and liquid systems described above may each be packaged separately, prior to being mixed into a hardening composition shortly before use. However, components of the hardening composition may be combined in one package and, in a preferred embodiment, a hardening composition is mixed and delivered in a capsule. The capsule may be a standard capsule for delivery of hardening compositions, such as those used in the dental and medical industries.

In a preferred embodiment, the acidic copolymer, when pre-dissolved in water to form an aqueous solution, has a concentration of acidic copolymer of from 10 to 65% by weight. Concentrations of acidic copolymer of greater than 65% by weight are difficult to achieve due to the inherent solubility of the acidic copolymers in water. If, however, concentrations of less than 10% by weight of acidic copolymer are used, the working time and the setting time of a hardening composition and/or the mechanical properties of a corresponding glass ionomer may be deteriorated.

The weight ratio of acidic polymer to particulate glass is suitably from 0.1:1 to 0.5:1, preferably 0.2:1 to 0.4:1; and the weight ratio of water to glass is preferably 0.4:1 to 0.1:1. In a preferred embodiment, the acidic copolymer in anhydrous form accounts for 0 to 25% by weight, more preferably 8 to 15% by weight, of the hardening composition. If the amount of acidic copolymer used in the hardening composition is outside this range, the setting time of a hardening composition and/or the mechanical properties of a corresponding ionomer cement may be deteriorated.

The reaction of the polyacid and glass preferably may be carried out in the presence of a setting retarder. The setting retarder may be present in amounts sufficient as to modify the working time (that is, the time taken from the start of mixing of the acidic copolymer, particulate glass and water, to the time when the mixture became rubber-like and unworkable) and/or setting time of the mixture, as required. Examples of setting retarders that may be used, either singly or in combination, in the following invention include chelating agents such as tartaric acid, citric acid, malic acid, itaconic acid, aconitic acid, maleic acid, mellitic acid, tricarballylic acid or derivatives thereof comprising at least one hydroxyl group, multivalent metal chelating agents such as beta-diketones, including acetyl acetonate, or ethylene diamine tetraacetic acid.

In a preferred embodiment, tartaric acid is employed as a setting retarder, preferably as an aqueous solution of 0 to 12% by weight. Alternatively, tartaric acid is employed as a setting retarder in anhydrous form, preferably as a component of an admixture, wherein the concentration of said retarder in the powder is 0 to 5% by weight. If tartaric acid is used as an aqueous solution in concentrations of greater than 12% by weight or in an admixture in concentrations of greater than 5% by weight, the setting time of the mixture may be increased to such an extent that the hardening composition is of no practical use.

The hardening compositions of the present invention may be kneaded or mixed with pigments, bacteriostatic or antibiotic agents, fillers, or natural or synthetic resins, either singly or in combination.

In a preferred embodiment, the hardening composition comprises a pigment or pigments. Suitable organic and inorganic colour pigments may be selected from a list which includes, but is not restricted to, titanium oxide, iron oxide, Hansa Yellow, chrome yellow, Phthalocyanine Blue and carbon black, moisture resistant pigments such as clay, talc, calcium carbonate, silica powder and silica gel, and pigment dispersions prepared so as to be easily dispersible in copolymer solutions. These pigments are added in order to colour the materials to be coated. Such pigments may be present in the hardening composition in amounts of up to 2% by weight.

Bacteriostatic agents or antibiotics may be added to the cement powder in minor amounts, as desired, to provide antibacterial or anticariogenic activity in use, particularly when used as a dental restorative. Examples of suitable bacteriostatic or antibiotic agents include, but are not restricted to chlorhexadine, chlorinated phenols, phenols, quaternary amine salts, silver ions, copper ions or colloidal silver, either singly or in combination.

Fillers may be added to the hardening composition in minor amounts, as desired, to provide a glass ionomer composite. Examples of suitable fillers include, but are not restricted to nanoparticles, flakes, whiskers, fibers, dumbbell shaped particles, spherical particles, agglomerates, woven unities and braided unities, either singly or in combination. Suitable fillers further comprise inert fillers which include, but are not restricted to glasses, asbestos, plastics, ceramics and metals, either singly or incombination.

Resins or polymers may be added to the hardening composition in minor amounts, as desired, to provide a glass ionomer composite. Examples of suitable resins or polymers include, but are not restricted to natural resins or natural polymers such as cellulose, pectin, chitin, lignin, collagen, latex, caoutchouc or rubber, or; synthetic resins or synthetic polymers such as synthetic rubbers, nitrile rubbers or polyamide resins, either singly or in combination.

The hardening composition of the present invention, when hardened, provides a glass ionomer with improved mechanical properties such as biaxial flexural strength, fracture toughness and compressive strength. In a preferred embodiment, the hardening composition of the invention, when set, has a fracture toughness, $K_{Ic}$, when measured as described in the Examples, of preferably greater than 0.6 MPa·m$^{1/2}$, more preferably greater than 0.8 MPa·m$^{1/2}$, most preferably greater than 1.0 MPa·m$^{1/2}$, and/or a biaxial flexural strength of more than 45 MPa, preferably more than 60 MPa, more preferably more than 65 MPa.

It is additionally preferred that the hardening composition, when set, has an opacity towards X-rays equivalent to at least 1.5 mm aluminum/mm of hardened glass ionomer, preferably at least 2.0 mm Al/mm.

Such properties render the hardening composition suitable for use in a variety of fields. In a preferred embodiment, the hardening composition is suitable for dental use. The hardening composition may find application in dental restoration as a dental ionomer cement suitable, for example, for the filling or obturation of dental cavities or fissures, the reconstruction of teeth, core build-up or the luting of dental bridges. In addition to traditional dental use, the hardening compositions of the present invention may also find application in preventive dentistry as, for example, pit and fissure sealants, and as fillers for cervical lesions.

The uses of the hardening compositions of the present invention are not limited to dentistry, but are also suitable for use in medical disciplines. For example, the hardening compositions are suitable for use in surgery, particularly orthopaedic surgery, where they may be used to assist in the resetting of fractured bone material, and in grouting compositions.

The hardening composition may be applied to a tooth or other surface by any convenient means. Generally, the mixed material is taken up onto a small spatula and pressed into a cavity or onto a surface. Another common method of use is to apply the material directly into a cavity or onto a surface from a suitable syringe, capsule or other hand-held dental appliance such as a hand-gun, more specifically, a dental hand-gun. In addition to the use of pressure for the application of the hardening composition to the cavity or surface, mechanical or ultrasound vibration may also be employed.

The hardening composition, thus applied, can then be formed to the desired shape using any convenient means. Generally the range of tools available to the dentist or dental technician for the filling of cavities, luting and related dental reconstruction procedures will suffice for shaping of the glass ionomer.

In order that the invention may be well understood, the following Examples are given by way of example only. In the Examples all percentages are by weight unless otherwise stated.

EXPERIMENTAL PART

1. Particulate Glass Formation

Glasses with the compositions given in the following table were either obtained from commercial sources, or were smelted in an electrical furnace at 1400 to 1500° C. The procedure for smelting one glass (Example 1) is given below, and other glasses not obtained commercially were made analogously using appropriate ingredients.

Example 1

The following materials by weight were added together. Silica (25.8 parts), aluminum oxide (23.4 parts), zinc oxide (25.0 parts), phosphorus pentoxide (16.4 parts), and calcium fluoride (20.4 parts). The mixture was placed in a glass bottle and tumbled for one hour to thoroughly mix the components together. The mixture was then transferred to an aluminum oxide crucible and heated at a rate of 200° C./min to 700° C. to allow degassing and moisture loss. After ten minutes at 700° C. the mixture was heated at 200° C./min to 1400° C. and held at this temperature for 120 minutes, then the temperature was increased at 200° C./min to 1500° C. and held at this temperature for 30 minutes. The oven was then opened, the crucible was withdrawn, and the molten glass was poured directly into cold water to give broken glass fragments.

| Composition of the glasses referred to, in % by weight | | | |
|---|---|---|---|
| Element | Zn glass | Ca G338 glass | Sr G200 glass |
| $SiO_2$ | 21-23 | 27.8 | 32.1 |
| $Al_2O_3$ | 23-25 | 31.3 | 24.6 |
| $Na_2O$ | <1.0 | 10.6 | 2.9 |
| CaO | 5-6 | 10.8 | — |
| SrO | 13-15 | — | 28.7 |
| ZnO | 14-17 | — | — |
| F | 4.5-6-5 | 14.8 | 12.3 |
| $P_2O_5$ | 15-17 | 7.0 | 4.8 |
| $As_2O_3$ | | <2 ppm | <2 ppm |
| PbO | | <50 ppm | <50 ppm |
| total heavy metals | <0.3 | | |

2. Reduction in Particle Size of Particulate Glass

The glass, whether smelted as above or obtained commercially, was first milled if necessary in a dry ball mill to give powder with a mean particle size, D50, under about 100 µm. This powder was then further milled in water slurry to give a particulate glass powder with a mean particle size, D50, of approximately 3 µm. A portion of this particulate glass was further milled to give glass powder with a mean particle size, D50, of approximately 1 µm. Particle size measurements were made an a Malvern Particle Master Sizer model S. Because the reactivity of the glass particles depends on their size and surface area, it is important that particle size is carefully controlled.

3. Acidic Copolymer Formation

Acidic copolymers with the compositions and molecular weights disclosed herein were either obtained from commercial sources, or were formed by copolymerisation of acrylic acid with a selected monomer or monomers and/or additives, in the ratios specified, at room temperature. Room temperature refers to 23±1° C. at 50±10% humidity. The viscosities of the resultant solutions (and of the glass ionomer liquids described below) were measured using a Bohlin CS 50 viscometer and are reported in units of Pa.s at 23° C. The procedures used for copolymerizing such mixtures are presented in Examples 2 to 13, and other acidic copolymers not obtained commercially were made analogously using appropriate ingredients.

Example 2

Acrylic Acid-Itaconic Acid Copolymer with a 2% Itaconic Acid Portion

Under an inert atmosphere a mixture of 96.5 mL of acrylic acid, 125 mL of deionised water, 3.78 g of itaconic acid and 20 mL of isopropanol and a solution of 1.19 g of potassium persulfate in 75 mL of water were added simultaneously over a period of 1 h at 95° C. to a stirred solution of 1.92 g of potassium persulfate in 400 mL of water. The reaction mixture was kept under reflux for an additional 2 h to complete the reaction before 213 mL of water were removed under reduced pressure. The resulting polyacid was found to have mean molecular weights, $M_w$ of 54000 g/mol and $M_n$ of 9500 g/mol.

Example 3

Acrylic Acid-Itaconic Acid Copolymer with a 3% Itaconic Acid Portion

Under an inert atmosphere a mixture of 306 mL of acrylic acid, 600 mL of deionised water, 1.27 g potassium persulfate, 17.90 g of itaconic acid and 44 mL of isopropanol was added continuously over a period of 2 h at 95° C. to a stirred solution of 1.27 g of potassium persulfate in 190 mL of water. The reaction mixture was kept under reflux for an additional 2 h to complete the reaction before 450 mL of water were removed under reduced pressure. The resulting polyacid was found to have mean molecular weights, $M_w$ of 120000 g/mol and $M_n$ of 18000 g/mol.

Example 4

Acrylic Acid-Itaconic Acid Copolymer with a 3% Itaconic Acid Portion

Under an inert atmosphere a mixture of 160 mL of acrylic acid, 300 mL of deionised water, 0.62 g potassium persulfate, 8.95 g of itaconic acid and 47.4 mL of isopropanol was added continuously over a period of 2 h at 95° C. to a stirred solution of 0.62 g of potassium persulfate in 95 mL of water. The reaction mixture was kept under reflux for an additional 2 h to complete the reaction before 240 mL of water were removed under reduced pressure. The resulting polyacid was found to have mean molecular weights, $M_w$ of 99000 g/mol and $M_n$ of 17000 g/mol.

Example 5

Acrylic Acid-Itaconic Acid Copolymer with a 3% Itaconic Acid Portion

Under an inert atmosphere a mixture of 84 mL of acrylic acid, 20 mL of deionised water, 394 mg of AIBN, 4.68 g of itaconic acid and 1.80 g of mercapto succinic acid was added continuously over a period of 1 h at 95° C. under stirring to 110 mL of water. The reaction mixture was kept under reflux for an additional 2 h to complete the reaction before 28 mL of water were removed under reduced pressure. The resulting polyacid was found to have mean molecular weights, $M_w$ of 53000 g/mol and $M_n$ of 13000 g/mol.

Example 6

Acrylic Acid-Itaconic Acid Copolymer with a 5% Itaconic Acid Portion

Under an inert atmosphere a mixture of 149.5 mL of acrylic acid, 300 mL of deionised water, 0.62 g potassium persulfate, 14.92 g of itaconic acid and 22 mL of isopropanol was added continuously over a period of 2 h at 95° C. to a stirred solution of 0.62 g of potassium persulfate in 95 mL of water. The reaction mixture was kept under reflux for an additional 2 h to complete the reaction before 217 mL of water were removed under reduced pressure. The resulting polyacid was found to have mean molecular weights, $M_w$ of 120000 g/mol and $M_n$ of 16000 g/mol.

Example 7

Acrylic Acid-Itaconic Acid Copolymer with a 7% Itaconic Acid Portion

Under an inert atmosphere a mixture of 146.4 mL of acrylic acid, 300 mL of deionised water, 0.62 g potassium persulfate, 20.89 g of itaconic acid and 22 mL of isopropanol was added continuously over a period of 2 h at 95° C. to a stirred solution of 0.62 g of potassium persulfate in 95 mL of water. The reaction mixture was kept under reflux for an additional 2 h to complete the reaction before 214 mL of water were removed under reduced pressure. The resulting polyacid was found to have mean molecular weights, $M_w$ of 150000 g/mol and $M_n$ of 21000 g/mol.

Example 8

Acrylic Acid-Itaconic Acid Popolymer with a 10% Itaconic Acid Portion

Under an inert atmosphere a mixture of 142 mL of acrylic acid, 300 mL of deionised water, 0.62 g potassium persulfate, 29.84 g of itaconic acid and 22 mL of isopropanol was added continuously over a period of 2 h at 95° C. to a stirred solution of 0.62 g of potassium persulfate in 95 mL of water. The reaction mixture was kept under reflux for an additional 2 h to complete the reaction before 210 mL of water were removed under reduced pressure. The resulting polyacid was found to have mean molecular weights, $M_w$ of 140000 g/mol and $M_n$ of 19000 g/mol.

Example 9

Acrylic Acid-Itaconic Acid Copolymer with a 10% Itaconic Acid Portion

Under an inert atmosphere a mixture of 88.9 mL of acrylic acid, 125 mL of deionised water, 18.9 g of itaconic acid and 20 mL of isopropanol and a mixture of 1.23 g of azobis(4-cyano valeric acid), 18 mL of water and 57 mL of ethanol were added simultaneously over a period of 1.5 h at 95° C. to a stirred solution of 1.23 g of azobis(4-cyano valeric acid) in 250 mL of water. The reaction mixture was kept under reflux for an additional 3 h to complete the reaction before 280 mL of water, ethanol and isopropanol were removed under reduced pressure. The resulting polyacid was found to have mean molecular weights, $M_w$ of 66000 g/mol and $M_n$ of 8000 g/mol.

Example 10

Acrylic Acid-Itaconic Acid Copolymer with a 12% Itaconic Acid Portion

Under an inert atmosphere a mixture of 138.5 mL of acrylic acid, 300 mL of deionised water, 0.62 g potassium persulfate, 25.81 g of itaconic acid and 22 mL of isopropanol was added continuously over a period of 2 h at 95° C. to a stirred solution of 0.62 g of potassium persulfate in 95 mL of water. The reaction mixture was kept under reflux for an additional 2 h to complete the reaction before 210 mL of water were removed under reduced pressure. The resulting polyacid was found to have mean molecular weights, $M_w$ of 170000 g/mol and $M_n$ of 23000 g/mol.

Example 11

Acrylic Acid-2-hydroxyethyl Acrylic Acid Copolymer with a 3% 2-hydroxyethyl Acrylic Acid Portion Under an inert atmosphere a mixture of 48 mL of acrylic acid, 63 mL of deionised water, 2.53 g of 2-hydroxyethyl acrylic acid and 10 mL of isopropanol and a solution of 0.59 g of potassium persulfate in 38 mL of water were added simultaneously over a period of 1 h at 95° C. to a stirred solution of 0.59 g of potassium persulfate in 200 mL of water. The reaction mixture was kept under reflux for an additional 2 h to complete the reaction before 320 mL of water were removed under reduced pressure. The resulting polyacid was found to have mean molecular weights, $M_W$ of 70000 g/mol and $M_n$ of 9000 g/mol.

Example 12

Acrylic Acid-2-hydroxyethyl Acrylic Acid Copolymer with a 10% 2-hydroxyethyl Acrylic Acid Portion Under an inert atmosphere a mixture of 44.5 mL of acrylic acid, 63 mL of deionised water, 8.44 g of 2-hydroxyethyl acrylic acid and 10 mL of isopropanol and a solution of 0.59 g of potassium persulfate in 38 mL of water were added simultaneously over a period of 1 h at 95° C. to a stirred solution of 0.59 g of potassium persulfate in 200 mL of water. The reaction mixture was kept under reflux for an additional 2 h to complete the reaction before 320 mL of water were removed under reduced pressure. The resulting polyacid was found to have mean molecular weights, $M_w$ of 69000 g/mol and $M_n$ of 9500 g/mol.

Example 13

Acrylic Acid-2-hydroxyethyl Acrylic Acid Copolymer with a 15% 2-hydroxyethyl Acrylic Acid Portion Under an inert atmosphere a mixture of 42 mL of acrylic acid, 163 mL of deionised water, 12.65 g of 2-hydroxyethyl acrylic acid and 10 mL of isopropanol and a solution of 0.59 g of potassium persulfate in 38 mL of water were added simultaneously over a period of 1 h at 95° C. to a stirred solution of 0.59 g of potassium persulfate in 200 mL of water. The reaction mixture was kept under reflux for an additional 2 h to complete the reaction before 320 mL of water were removed under reduced pressure. The resulting polyacid was found to have mean molecular weights, $M_w$ of 67000 g/mol and $M_n$ of 8000 g/mol.

4. Determination of Mean Molecular Weights, $M_n$ and $W_w$, of Acidic Copolymers The mean molecular weights, $M_n$ and $M_w$ and molecular weight distributions of the acidic copolymers disclosed herein were determined using the gel permeation chromatography (GPC) analysis method described below. $M_n$ refers to the number-mean molecular weight and $M_w$ refers to the weight-mean molecular weight. All mean molecular weights, $M_n$ and $M_w$ are reported in values of g/mol.

a. Analysis conditions:

| Analysis conditions: | |
|---|---|
| Eluant: | 11.88 g/L $Na_2HPO_4$ in deionised water |
| Precolumn: | PSS Suprema, 10 µm, 30 Å, ID 8 mm × 50 mm |
| Columns: | PSS Suprema, 10 µm, 30 Å, ID 8 mm × 300 mm |
| | PSS Suprema, 10 µm, 1000 A, ID 8 mm × 300 mm |
| Pump: | Agilent 1100 HPLC Pump |
| Flow Rate: | 1.0 mL/min |
| Injection system: | Agilent 1100 autosampler with 50 pL injection volume |
| Sample concentration: | 3.0 g/L |
| Temperature: | 23° C. |
| Detectors: | Agilent 1100 UV at 230 nm |
| | Agilent 1100 differential refractometer |
| Analysis: | PSS-WinGPC Unity Version 7.2 | b. Sample Preparation:
The samples of acidic copolymers were weighed out exactly, mixed with a defined volume of 11.88 g/L $Na_2HPO_4$ in deionised water and dissolved at room temperature. The samples of acidic copolymers were fully dissolved after only a short time. The sample solutions of acidic copolymers were filtered through a 1.0 µm disposable filter and 50 µL was injected for GPC analysis. GPC analysis furnished elution profile results for each sample.

c. Calibration and Analysis:
A calibration curve for the column combination was first established by GPC analysis using sodium polyacrylate standards PAA. The mean molecular weights, $M_n$ and $M_w$, and molecular weight distributions of the samples of acidic copolymers were calculated by computer integration from the elution profile results obtained in step 2, based on the sodium polyacrylate PAA calibration curve.

5. Formation of Aqueous Solutions of Copolymers (Glass Ionomer Liquids)

The acidic copolymers were dissolved in water to form aqueous solutions of acidic copolymers for use in the formation of hardening compositions. Aqueous acidic copolymer solutions which additionally comprise a setting retarder were also produced and hereinafter are referred to as glass ionomer liquids. The compositions and procedures used for the formation of such solutions (glass ionomer liquids) are presented in Examples 14 to 19.

Example 14

Tartaric acid (0.75 g) was added to 14.44 g of the aqueous polyacid solution of Example 4. The mixture was stirred for 1 h at room temperature before 0.19 g of water was removed under reduced pressure. The resulting glass ionomer liquid had a polyacid content of 41% by weight and a tartaric acid content of 5% by weight.

Example 15

Tartaric acid (2.40 g) and water (12.82 g) were added to 14.78 g of the aqueous polyacid solution of Example 4 and the mixture was stirred for 1 h at room temperature to give a glass ionomer liquid having a polyacid content of 21% by weight and a tartaric acid content of 8% by weight.

Example 16

Tartaric acid (2.40 g) and water (10.00 g) were added to 17.60 g of the aqueous polyacid solution of Example 4 and the mixture was stirred for 1 h at room temperature to give a glass ionomer liquid having a polyacid content of 25% by weight and a tartaric acid content of 8% by weight.

Example 17

Tartaric acid (1.20 g) and water (0.58 g) were added to 18.22 g of the aqueous polyacid solution of Example 6 and the mixture was stirred for 1 h at room temperature to give a glass ionomer liquid having a polyacid content of 40% by weight and a tartaric acid content of 6% by weight.

Example 18

Tartaric acid (1.20 g) and water (0.54 g) were added to 18.26 g of the aqueous polyacid solution of Example 7 and the mixture was stirred for 1 h at room temperature to give a glass ionomer liquid having a polyacid content of 40% by weight and a tartaric acid content of 6% by weight.

Example 19

Tartaric acid (1.20 g) and water (0.28 g) were added to 18.52 g of the aqueous polyacid solution of Example 8 and the mixture was stirred for 1 h at room temperature to give a glass ionomer liquid having a polyacid content of 40% by weight and a tartaric acid content of 6% by weight.

6. Anhydrous Acidic Copolymer Formation

The acidic copolymers could be obtained in anhydrous form, as required for the formation of anhydrous admixtures comprising acidic copolymer and particulate glass. Two methods of formation of anhydrous acidic copolymers are presented in Examples 20 and 21.

Example 20

Under an inert atmosphere a mixture of 305 mL of acrylic acid, 600 mL of deionised water, 1.55 g potassium persulfate, 17.90 g of itaconic acid and 56 mL of isopropanol was added continuously over a period of 2 h at 95° C. to a stirred solution of 1.55 g of potassium persulfate in 190 mL of water. The reaction mixture was kept under reflux for an additional 2 h to complete the reaction before approx. 200 mL of water were removed under reduced pressure. This polyacid solution was pre-dried at 120° C. for 48 h to give solid polyacid, which was milled to a D50 of 33 μm and finally dried under high vacuum at 90° C. for 24 h.

Example 21

Under an inert atmosphere a mixture of 305 mL of acrylic acid, 600 mL of deionised water, 1.18 g potassium persulfate, 17.90 g of itaconic acid and 35 mL of isopropanol was added continuously over a period of 2 h at 95° C. to a stirred solution of 1.18 g of potassium persulfate in 190 mL of water. The reaction mixture was kept under reflux for an additional 2 h to complete the reaction before approx. 200 mL of water were removed under reduced pressure. This polyacid solution was pre-dried at 120° C. for 21 h to give solid polyacid, which was milled to a D50 of 35 μm and finally dried under high vacuum at 90° C. for 24 h.

7. Hardening Composition Formation

Hardening compositions with the compositions given in the table were formed by mixing particulate glasses with acidic copolymers, in the ratios specified, at 23° C. The compositions may be mixed by any convenient means, for instance (i) by hand using a pad (or other mixing surface) and spatula, or by using a mortar and pestle, or (ii) mechanically, for instance using a capsule and mechanical vibrator or ultrasonic vibrator, or using a mechanical mixing device. The procedures used for formation of such hardening compositions are presented in Examples 22 and 23.

Example 22

The glass powder with mean particle size of 3 μm (86.64 parts) was mixed with dried (anhydrous) acidic copolymer of either Example 20 or Example 21 (12.27 parts) and finely ground tartaric acid (1.09 parts). The components were tumbled together in a glass bottle for one hour to give a homogenous mixture. This powder mixture was transformed into a hardening composition by combining three parts by weight of the powder with 1 part by weight of a 40% by weight solution of acidic copolymer in water at 23° C.

Example 23

Glass powder (1.65 parts by weight) was combined at 23° C. with 1 part by weight of an aqueous solution containing 40% by weight acidic copolymer and 12% by weight tartaric acid, and the two were spatulated together until a homogenous paste was obtained.

For each test method the working time (w.t.) was taken as the time from the start of mixing of the acidic copolymer, particulate glass and water, to the time when the mixture became rubber-like and unworkable. The working time is reported in units of minutes. The setting time (s.t.) was determined according to ISO 9917-1:2003 and is reported in units of minutes.

8. Hardened Glass Ionomers

Hardened glass ionomers formed after setting (hardening) of the hardening compositions disclosed in Examples 22 and 23, above, were examined with respect to the mechanical properties of each material. In general, samples were stored at 37° C. and at >95% humidity for one hour immediately after preparation, then stored in water at 37° C. for a further 23 hours, before being tested. Specifically, the compressive strength, fracture toughness $K_{Ic}$, and/or biaxial flexural strength were measured for each material. Physical properties of the hardened glass ionomers were measured according to ISO 9917-1:2003.

The compressive strength, c.s., was determined according to ISO 9917-1:2003 and is reported in units of MPa.

Fracture toughness, $K_{Ic}$, was measured at room temperature according to a literature method using the macro hardness testing machine DIA-TESTOR 7521 (Wolpert). After applying a load to the specimen the load was kept constant for 30 s. In a series of measurements the load was varied from, about 9.8 N (1 kilopont) to 2425.5 N (250 kilopont). At least two tests per specimen (minimum 12 for each material) were analyzed to determine the half length of the impression diagonal and the radial crack size (Palmqvist crack), which are essential values for the calculation of the stress intensity factor $K_I$. The size of the impressions and length of the Palmqvist cracks were measured using an optical microscope. The fracture toughness, $K_{Ic}$, was calculated using a standard equation and is reported in units of MPa·m$^{1/2}$. Full details of the method are given in (i) K. Niihara, R. Morena, D. P. H. Hasselman, Evaluation of $K_{Ic}$ of brittle solids by the indentation method with low crack-to-indent ratios. J. Mater. Sci. Lett, 1 (1982) 13, and (ii) M. T. Laugier, New formula for indentation toughness in ceramics, J. Mater. Sci. Lett. 6 (1987) 355.

The biaxial flexural strength values given were measured on discs 20 cm diameter and 1 mm thick, with a supporting knife edge ring support of 15 mm diameter and a pin diameter of 3 mm. The strength values were measured using a Zwick universal testing machine and are reported in MPa. The method is described, for example, in ASTM F 394, and by Williams, Billington and Pearson in Dental Materials 2002, July, 18 (5), 376 to 379.

The opacity towards X-rays was determined according to ISO 9917-1:2003. The opacity towards X-rays was measured for hardened glass ionomer samples and is expressed in units of mm of aluminium equivalent to 1.0 mm of hardened glass ionomer.

9. Results and Discussion

The outcome of the experiments performed are discussed below, with reference to the results presented in Tables 1 to 5.

It has been found that by using a combination of a specially developed particulate glass and a specially developed acidic copolymer of a specific composition and molecular weight range, the biaxial flexural strength of the resulting glass ionomer can be increased to over 70 MPa. As demonstrated in the following tables, this increase of almost 80% over previously known glass ionomer materials is only possible by use of the optimized glass together with the polymer compositions. Furthermore, the fracture toughness, $K_{Ic}$, of the resulting glass ionomer may be increased to 1.30 MPa·m$^{1/2}$.

In Tables 1, 2 and 5, the p/l ratio refers to the ratio of powder to liquid by weight.

In the Tables 1, 2, and 3, the glass types Zn, Sr, and Ca refer to the compositions below, wherein the glass designated Zn is the glass of this invention, and those designated Ca and Sr are conventional glasses used for many years in commercial glass ionomer formulations. The glass ionomer formulation of this invention may also comprise components which act as reaction retarders, accelerators, or pigmentation, as is common in such formulations.

It has been shown that in combination with the glass of this invention, the biaxial flexural strength of the resulting glass ionomer may be increased by increasing one or both of the concentration and molecular weight of the acid. For example, in Table 1, experiment pairs 2-3 and 5-6 illustrate that changing the tartaric acid concentration has no effect on the biaxial flexural strength, but that increasing the acid concentration from 30% to 35% brings an increase in strength from 34 MPa to 41 MPa. Experiment numbers 19 and 20 illustrate that an increase in molecular weight also brings about an increase in biaxial flexural strength.

The experiment numbers 1 to 8 in Table 1 all use 100% poly-acrylic acid with concentrations between 30% and 35% and a molecular weight of about 50000, and reach a biaxial flexural strength between about 34 MPa and 49.5 MPa. It is seen from Table 3 that such polymer solutions are stable up to at least 15 months of age. In contrast, a pure poly-acrylic acid solution with a concentration of 40% was not stable and gelled after nine months. It is know to those skilled in the art that increasing the molecular weight of a polyacid also increases its tendency to gel. Therefore, as long as 100% acrylic acid polymer is used it is not possible to increase the acid concentration or molecular weight further in order to increase the biaxial flexural strength, because the resulting polyacid solution is not physically stable and gels over time.

It is known from the prior art (Wilson et al. J. Dent. Res, 1975, 54 (6), 1173) that adding small amounts of a comonomer to the polymer can greatly decrease the tendency of a polymer solution to gel. Data in Table 3 shows that adding even only 1% of itaconic acid as a comonomer allows a stable solution with a concentration of 49% and a mean molecular weight of 72000 to be produced. Increasing the amount of itaconic acid comonomer to 10% allows a stable solution with a concentration of 50% and a mean molecular weight of 122000 to be made.

Experiment numbers 29 and 31 show that the biaxial flexural strength increases as the mean molecular weight of the acidic copolymer increases, while experiment numbers 31 and 32 show that the biaxial flexural strength increases as the mean size of the particulate glass decreases, while experiment numbers 32 and 33 again illustrate the increase in biaxial flexural strength with increase in mean molecular weight. The comparative experiment numbers 34 to 37 illustrate that the high biaxial flexural strength values are only possible with the glass of this invention; the conventional glasses are too fast when milled to the small size possible with the glass of this invention, and when used with a larger mean particle size give inferior strength values. Finally, comparative experiment numbers 38 to 40 show that the biaxial flexural strength of the glass ionomer of the present invention are higher than those of typical commercially available glass ionomers.

TABLE 1

Results using particulate Zn glass with poly acrylic acid and acrylic-itaconic acid copolymer (mean molecular weight, $M_w$, 50000)

| Expt. no. | Glass type | D50 glass (μm) | p/l ratio | Polyacid (%) | AA/IA ratio | TAA conc. (%) | w.t. (min) | s.t. (min) | biaxial flex. str. (MPa) |
|---|---|---|---|---|---|---|---|---|---|
| 1 | Zn | 3.0 | 2.2 | 35.0 | 100/0 | 6.00 | 4.39 | 3.44 | 44.11 |
| 2 | Zn | 1.0 | 1.85 | 30.0 | 100/0 | 12.00 | 1.50 | 2.33 | 34.09 |
| 3 | Zn | 1.0 | 1.85 | 30.0 | 100/0 | 9.00 | 1.25 | 2.33 | 34.45 |
| 4 | Zn | 2.8 | 2.40 | 35.0 | 100/0 | 9.00 | 2.75 | 3.58 | 35.29 |
| 5 | Zn | 1.0 | 1.85 | 35.0 | 100/0 | 9.00 | 1.50 | 2.33 | 41.20 |

TABLE 1-continued

Results using particulate Zn glass with poly acrylic acid and acrylic-
itaconic acid copolymer (mean molecular weight, $M_w$, 50000)

| Expt. no. | Glass type | D50 glass (μm) | p/l ratio | Polyacid (%) | AA/IA ratio | TAA conc. (%) | w.t. (min) | s.t. (min) | biaxial flex. str. (MPa) |
|---|---|---|---|---|---|---|---|---|---|
| 6 | Zn | 1.0 | 1.85 | 35.0 | 100/0 | 12.00 | 1.75 | 2.67 | 41.63 |
| 7 | Zn | 2.8 | 2.40 | 35.0 | 100/0 | 12.00 | 2.67 | 3.33 | 42.51 |
| 8 | Zn | 3.0 | 2.40 | 35.0 | 100/0 | 12.00 |  |  | 49.50 |
| 9 | Zn | 2.0 | 2.2 | 50.0 | 98/2 | 0.00 | 2.33 | 5.50 | 59.71 |
| 10 | Zn | 1.0 | 1.8 | 47.0 | 98/2 | 6.00 | 3.61 | 3.14 | 52.9 |
| 11 | Zn | 2.0 | 2.2 | 47.0 | 98/2 | 6.00 | 2.36 | 2.89 | 65.89 |
| 12 | Zn | 1.7 | 2.0 | 44.0 | 97/3 | 3.00 | 2.17 | 4.17 | 58.58 |
| 13 | Zn | 1.7 | 2.2 | 44.0 | 97/3 | 6.00 | 1.36 | 2.78 | 58.27 |
| 14 | Zn | 3.0 | 2.0 | 44.0 | 97/3 | 6.00 | 1.86 | 2.72 | 52.56 |
| 15 | Zn | 3.0 | 1.8 | 44.0 | 97/3 | 6.00 | 2.06 | 2.75 | 53.34 |
| 16 | Zn | 1.7 | 2.0 | 44.0 | 97/3 | 3.00 | 1.42 | 2.58 | 60.75 |
| 17 | Zn | 3.0 | 2.4 | 47.0 | 90/10 | 0.00 | 1.92 | 4.92 | 65.13 |
| 18 | Zn | 3.0 | 1.8 | 35.0 | 90/10 | 12.00 | 3.92 | 3.31 | 52.30 |

TABLE 2

Results using Zn, Sr, and Ca glasses and acidic copolymers with various acrylic/itaconic
acid ratios and mean molecular weights (copolymer content 40 wt %).

| Expt no. | Glass type | D50 glass (μm) | p/l ratio | AA/IA ratio | mean $M_w$ (g/mol) | TAA conc (%) | w.t. (min) | s.t. (min) | biaxial flex. str. (MPa) | c.s. (MPa) |
|---|---|---|---|---|---|---|---|---|---|---|
| 19 | Zn | 3 | 2.2 |  | 42000 |  |  |  | 48 |  |
| 20 | Zn | 3 | 2.2 |  | 68000 |  |  |  | 68 |  |
| 21 | Zn | 3 | 2.2 | 95/5 | 79000 | 6 | 2.19 | 2.55 | 66 | 224 |
| 22 | Sr | 2.9 | 2.2 | 95/5 | 79000 | 6 | 1.58 | 1.81 | 51 | 205 |
|  | Zn | 1.7 | 2.2 | 95/5 | 79000 |  | 1.92 | 2.75 | 60 | 234 |
| 23 | Zn | 3 | 2.2 | 90/10 | 122000 | 6 | 1.92 | 2.39 | 60 | 231 |
| 24 | Sr | 2.9 | 2.2 | 90/10 | 122000 | 6 | 1.44 | 1.92 | 50 | 197 |
| 25 | Zn | 1.7 | 2.0 | 90/10 | 122000 | 6 | 2.72 | 3.33 | 65 | 232 |
| 26 | Zn | 1.7 | 2.2 |  | 42000 |  | 1.36 | 2.78 | 58 | 207 |
| 27 | Zn | 1.7 | 2.2 |  | 68000 |  | 2.11 | 4.28 | 56 | 208 |
| 28 | Zn | 1.7 | 2.2 | 90/10 | 122000 | 6 | 2.25 | 2.92 | 71 | 240 |
| 29 | Zn | 1.7 | 2.2 | 97/3 | 128000 | 6 | 1.63 | 2.78 | 73 | 238 |
| 30 | Zn | 1.7 | 2.2 | 97/3 | 137000 | 6 | 1.83 | 2.67 | 70 | 223 |
| 31 | Zn | 1.7 | 2.2 | 97/3 | 99000 | 6 | 1.78 | 2.61 | 68 | 235 |
| 32 | Zn | 3 | 2.2 | 97/3 | 99000 | 6 | 1.47 | 2.28 | 59 | 221 |
| 33 | Zn | 3 | 2.2 | 93/7 | 150100 | 6 | 1.97 | 2.22 | 62 | 229 |
| 34 | Sr | 1.7 | 2.2 | 93/7 | 150100 | 6 | # | # | — | — |
| 35 | Ca | 1.7 | 2.2 | 93/7 | 150100 | 6 | # | # | — | — |
| 36 | Sr | 2.9 | 2.2 | 93/7 | 150100 | 6 | 1.61 | 2.5 | 52 | 209 |
| 37 | Ca | 5.5 | 2.2 | 93/7 | 150100 | 6 | 1.77 | 2.44 | 56 | 182 |
|  | Commercial product CF |  |  |  |  |  |  |  | 45 | 200 |
| 38 | Commercial product KME |  |  |  |  |  |  |  | 58 | 224 |
| 39 | Commercial product FGP |  |  |  |  |  |  |  | 49 | 215 |
| 40 | Commercial product IM |  |  |  |  |  |  |  | 53 | 202 | too fast to measure

TABLE 3

Viscosity and stability of various polymers/concentrations

| Acrylic/ Itaconic acid ratio | Concentration (% by weight) | mean $M_w$ (g/mol) | Viscosity (Pa·s at 23° C.) | stability |
|---|---|---|---|---|
| 100/0 | 35 | 53000 | 0.80 | Stable after 15 months |
| 100/0 | 45 | 53000 | nd | Gelled after 9 months |
| 100/0 | 50 | 53000 | 8.50 | Gelled after 9 months |
| 100/0 | 55 | 53000 | n.d. | Gelled after 1 month |
| 99/1 | 49 | 72000 | 12.95 | Stable after 24 months |
| 98/2 | 50 | 60000 | 7.05 | Stable after 24 months |

TABLE 3-continued

Viscosity and stability of various polymers/concentrations

| Acrylic/<br>Itaconic<br>acid ratio | Concentration<br>(% by weight) | mean $M_w$<br>(g/mol) | Viscosity<br>(Pa · s at 23° C.) | stability |
|---|---|---|---|---|
| 97/3 | 43 | 43000 | 2.60 | Stable after 12 months |
| 97/3 | 44 | 56000 | 3.75 | Stable after 12 months |
| 93/7 | 50 | 53000 | 5.88 | Stable after 23 months |
| 90/10 | 51 | 52000 | 4.30 | Stable after 25 months |
| 90/10 | 49 | 52000 | 2.45 | Stable after 24 months |
| 90/10 | 50 | 122000 | 14.73 | Stable after 24 months |
| 90/10 | 49 | 128000 | 9.83 | Stable after 24 months |
| 85/15 | 51 | 43000 | 3.75 | Stable after 23 months |

TABLE 4

Relative radioopacities

| Glass type | X-ray opacity (mm of aluminum equivalent to 1 mm of the hardened glass ionomer) | Highest biaxial flexural strength obtained (MPa) | Fracture toughness, Kic (MPa · m$^{1/2}$) |
|---|---|---|---|
| Zn | 2.2 | 73 | 1.30 |
| Sr | 2.3 | 52 | |
| Ca | 0.5 | 56 | |
| Commercial product KME | | | 0.50 |
| Commercial product IFM | | | 0.53 |
| Commercial product FGP | | | 0.40 |

Naturally, variations in the presentation of the glass ionomer material are possible without going outside the scope of the present invention. In experiment numbers 50 to 55 of Table 5, the acidic copolymer is dried, milled to 16 μm mean size (D50 dried polymer), and mixed with the particulate glass, which has a mean size (D50 glass) as shown. Experiment numbers 53 and 54 demonstrate that high biaxial flexural strengths of over 70 MPa may still be obtained by using the particulate glass and acidic copolymer of this invention.

TABLE 5

| Expt.<br>no. | D50<br>glass<br>(μm) | polymer in<br>powder (%<br>by weight) | p/l<br>ratio | w.t.<br>(min.) | s.t.<br>(min.) | c.s.<br>(MPa) | biaxial<br>flex. st.<br>(MPa) |
|---|---|---|---|---|---|---|---|
| 50 | 2.6 | 9 | 3.3 | 2.19 | 2.56 | 203 | 62 |
| 51 | 1.7 | 7 | 3.6 | 1.19 | 1.67 | 223 | 61 |
| 52 | 3.0 | 11 | 3.0 | 2.44 | 2.47 | 202 | 59 |
| 53 | 3.0 | 11 | 3.6 | 1.75 | 2.39 | 227 | 74 |
| 54 | 1.7 | 11 | 3.6 | 1.89 | 2.47 | 250 | 71 |
| 55 | 1.7 | 11 | 3.0 | 2.58 | 3.08 | 213 | 68 |

Liquid composition: 23% by weight acidic copolymer, 8% by weight TAA
Mean molecular weight, $M_w$: 120000
D50 dried polymer: 16 μm

The invention claimed is:
1. A hardening composition comprising
(i) a particulate glass and
(ii) an acidic copolymer reactive with the particulate glass under aqueous conditions, characterized in that said particulate glass comprises
a. 10-35% by weight of silica
b. 10-35% by weight of alumina
c. 3-30% by weight of zinc oxide
d. 4-30% by weight of $P_2O_5$
e. 3-25% by weight of fluoride, and
said acidic copolymer has a mean molecular weight, $M_w$, of from 50,000 to 200,000 and is obtainable by a process comprising the copolymerization of a mixture containing the following acids or hydrolysable derivatives thereof
(1) acrylic acid, and
(2) a compound of the following formula (II):

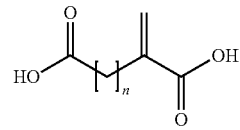

wherein n is an integer of from 1 to 3,
wherein said acidic copolymer has an acrylic acid to compound of formula II ratio between 98/2 and 85/15.

2. A hardening composition according to claim 1, wherein said particulate glass comprises
a. 20-25% by weight of silica
b. 20-25% by weight of alumina
c. 18-21% by weight of CaO plus SrO
d. 13-18% by weight of zinc oxide
e. 14-18% by weight of $P_2O_5$
f. 4-7% by weight of fluoride, and
wherein the content of $Na_2O$ is less than 1% by weight.

3. A hardening composition according to claim 1, wherein the mean particle size of the particulate glass is in the range of from 0.1 to 100 μm.

4. A hardening composition according to claim 1, wherein the mean particle size of the particulate glass is in the range of from 0.5 to 25 μm.

5. A hardening composition according to claim 1, wherein the mean particle size of the particulate glass is in the range of from 1 to 3.5 μm.

6. A hardening composition according to claim 1, wherein said acidic copolymer is a copolymer of acrylic acid and itaconic acid.

7. A hardening composition according to claim 6, wherein said acidic copolymer has a mean molecular weight, $M_w$, between 50000 and 200000.

8. A hardening composition according to claim 6, wherein said acidic copolymer has a mean molecular weight, $M_w$, between 75000 and 150000.

9. A hardening composition according to claim 6, wherein said acidic copolymer has a mean molecular weight, $M_w$, between 100000 and 130000.

10. A hardening composition according to claim 6, wherein said acidic copolymer has a mean molecular weight, between 5000 and 40000.

11. A hardening composition according to claim 6, wherein said acidic copolymer has a mean molecular weight, $M_n$, between 10000 and 30000.

12. A hardening composition according to claim 6, wherein said acidic copolymer has a mean molecular weight, $M_n$, between 15000 and 25000.

13. A hardening composition according to claim 1, which additionally comprises a setting retarder.

14. A hardening composition according to claim 13, wherein said setting retarder is tartaric acid.

15. A hardening composition according to claim 14, wherein the concentration of said acidic copolymer in water is 10 to 65% by weight.

16. A hardening composition according to claim 14, wherein the concentration of said retarder in water is 0 to 12% by weight.

17. A hardening composition according to claim 14, wherein the concentration of said retarder in the powder is 0 to 5% by weight.

18. A hardening composition according to claim 1, wherein the ratio by weight of the sum of zinc oxide and fluoride to $P_2O_5$ in the glass is from 0.8 to 3.0.

19. A hardening composition according to claim 1, wherein the ratio by weight of the sum of strontium oxide and zinc oxide to silica is from 1.0 to 1.95.

20. A hardening composition according to claim 1, wherein the ratio by weight of the sum of strontium oxide and zinc oxide to silica is from 1.25 to 1.6.

21. A hardening composition according to claim 20, wherein said acidic copolymer in anhydrous form accounts for 0 to 25% by weight of the composition.

22. A hardening composition according to claim 20, wherein said acidic copolymer in anhydrous form accounts for 8 to 15% by weight of the composition.

23. A hardening composition according to claim 1, wherein said particulate glass is provided mixed with the said acidic copolymer in anhydrous form.

24. A hardening composition according to claim 1, which when set has an opacity towards X-rays equivalent to at least 1.5 mm of aluminum per 1.0 mm of hardened glass ionomer.

25. A hardening composition according to claim 1, which further comprises a pigment or pigments.

26. A hardening composition according to claims 1 to 25, wherein the copolymer is a copolymer of an acidic polymerizable monomer having a moiety selected from a phosphonate group or a sulfonate group.

27. A hardening composition according to claims 1 to 26, which, when set, has a fracture toughness $K_{Ic}$, measured as described in the text, of greater than 0.6 $MPa \cdot m^{1/2}$ and/or a biaxial flexural strength of more than 45 MPa.

28. A hardening composition according to claims 1 to 26, which, when set, has a fracture toughness $K_{Ic}$, measured as described in the text, of greater than 0.8 $MPa \cdot m^{1/2}$ and/or a biaxial flexural strength of more than 45 MPa.

29. A hardening composition according to claim 27 or 28, wherein said composition is mixed and delivered in a capsule.

30. A hardening composition according to claim 27 or 28, wherein said composition is delivered as a powder and liquid system which can be mixed by hand.

31. A hardening composition according to claims 1 to 30, for dental use.

32. An aqueous polymer solution comprising 10 to 65% by weight of an acidic copolymer which is obtainable by the copolymerization of a mixture containing
   (1) acrylic acid, and
   (2) itaconic acid;
   wherein said acidic copolymer has an acrylic acid/itaconic acid ratio between 98/2 and 85/15, and a mean molecular weight, $M_w$, between 100000 and 130000.

* * * * *